US008200508B2

(12) United States Patent
Fujita et al.

(10) Patent No.: US 8,200,508 B2
(45) Date of Patent: Jun. 12, 2012

(54) IMAGE-DISPLAY DEVICE AND AN IMAGE-DISPLAY SYSTEM

(75) Inventors: Yasuhiko Fujita, Otawara (JP); Teruhiko Ebina, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 634 days.

(21) Appl. No.: 11/844,608

(22) Filed: Aug. 24, 2007

(65) Prior Publication Data

US 2008/0059244 A1 Mar. 6, 2008

(30) Foreign Application Priority Data

Aug. 29, 2006 (JP) .................................. 2006-232712

(51) Int. Cl.
*A61B 5/00* (2006.01)
(52) U.S. Cl. ................ 705/3; 705/2; 382/189; 382/309; 600/407
(58) Field of Classification Search .................. 705/2, 3; 424/9.3; 382/309; 1/1
See application file for complete search history.

(56) References Cited

U.S. PATENT DOCUMENTS

| | | | | |
|---|---|---|---|---|
| 5,740,801 | A | * | 4/1998 | Branson ........................ 600/407 |
| 6,941,323 | B1 | * | 9/2005 | Galperin ............................... 1/1 |
| 2002/0102211 | A1 | * | 8/2002 | Renshaw et al. ............... 424/9.3 |
| 2004/0076345 | A1 | * | 4/2004 | Olszak et al. .................. 382/309 |
| 2005/0025390 | A1 | * | 2/2005 | Tsujii ............................. 382/305 |
| 2007/0250491 | A1 | * | 10/2007 | Olszak et al. ..................... 707/3 |
| 2007/0255589 | A1 | * | 11/2007 | Rodriguez ........................ 705/2 |
| 2008/0010092 | A1 | * | 1/2008 | Smirniotopoulos et al. ...... 705/3 |
| 2008/0215630 | A1 | * | 9/2008 | Oosawa et al. ............ 707/104.1 |

FOREIGN PATENT DOCUMENTS

| | | |
|---|---|---|
| JP | 5-168654 | 7/1993 |
| JP | 2001-275986 | 10/2001 |
| JP | 2002-117137 | 4/2002 |
| JP | 2002-324230 | 11/2002 |
| JP | 2004-5364 | 1/2004 |
| JP | 2005-277558 | 10/2005 |
| JP | 2006-55507 | 3/2006 |

OTHER PUBLICATIONS

Google scholar search result.*
Google search results.*
Japanese Office Action issued Jun. 14, 2011, in Patent Application No. 2006-232712.

* cited by examiner

*Primary Examiner* — Dilek B Cobanoglu
(74) *Attorney, Agent, or Firm* — Oblon, Spivak, McClelland, Maier & Neustadt, L.L.P.

(57) ABSTRACT

From a database for reports, storage-location information paired with the characteristics information of this patient's medical image is searched. Then, the medical image stored in a storage location corresponding to the searched storage-location information is acquired, and this acquired medical image is simultaneously displayed with a patient's medical image. In this database, established-disease-name information that includes those with "no findings" or post-surgery-image-identifying information is stored by corresponding to the storage-location information, and the database is searched based on the established-disease-name information that indicates no findings or post-surgery-image-identifying information, and then corresponding medical images are acquired and simultaneously displayed with the patient's medical image.

13 Claims, 14 Drawing Sheets

FIG. 2
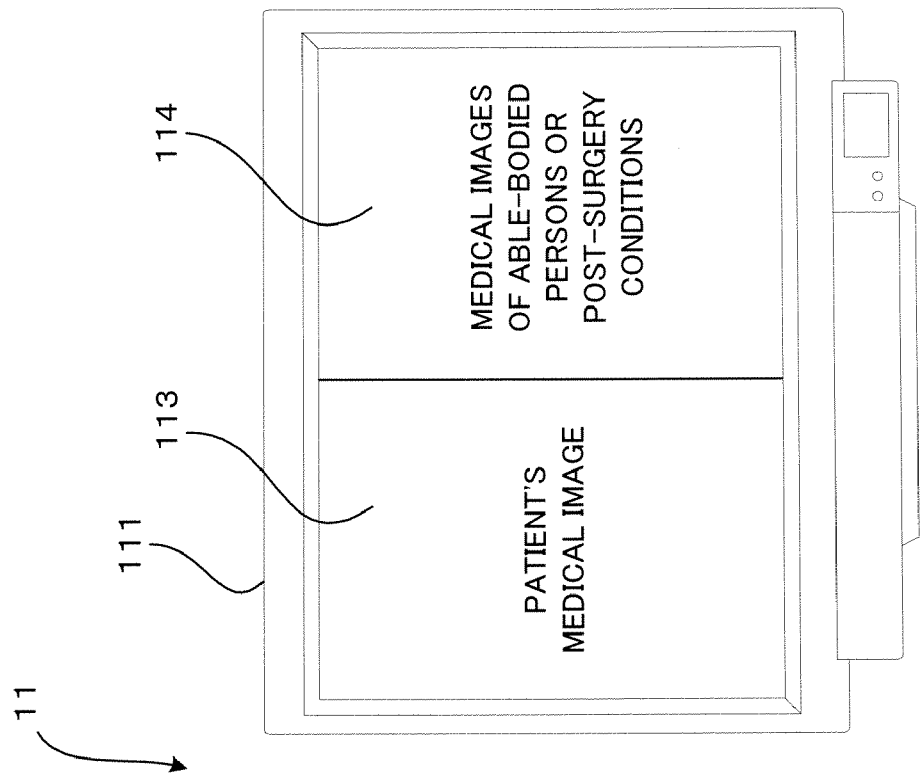
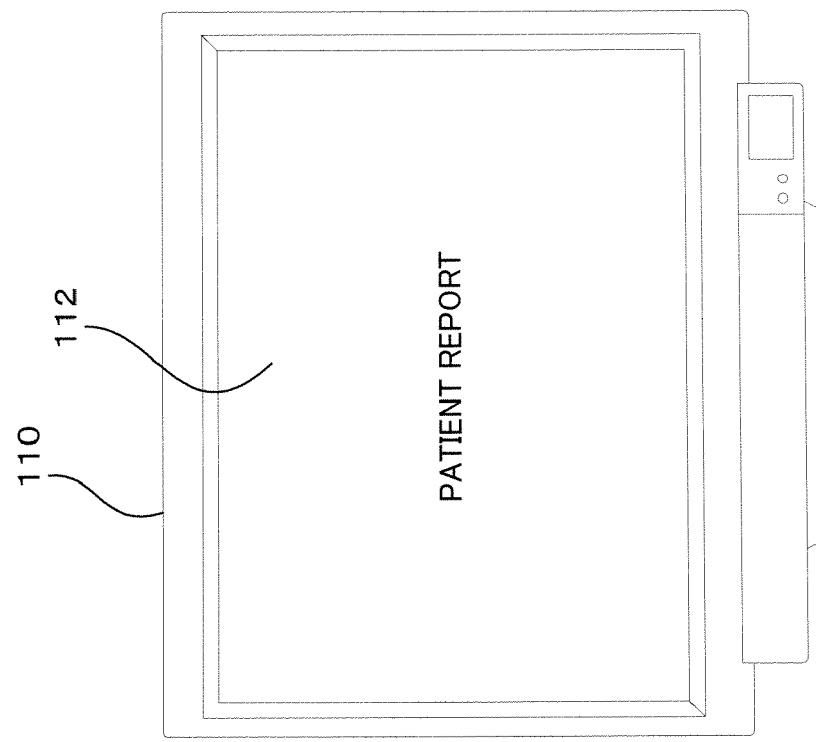

FIG. 5

| REPORT NUMBER | EXAMINATION DATE | PATIENT NAME | AGE | SEX | EXAMINATION TYPE | IMAGED SITE | DOCTOR | EXAMINATION PURPOSE | ESTABLISHED -DISEASE- NAME | STORAGE LOCATION |
|---|---|---|---|---|---|---|---|---|---|---|
| No.1001 | 2005/11/01 | Tanaka Tatsuya | 53 | MALE | PLAIN RADIOGRAPHY | CRURAL AREA | Tsuboi | EXAMINATION | LEFT FEMORAL FRACTURE | STORAGE UNIT20¥ IMAGE¥051101¥ IMAGE P |
| No.1002 | 2005/11/20 | Nakamura Shunsuke | 44 | MALE | X-RAY CT | CHEST | Miyamoto | EXAMINATION | LUNG CANCER | STORAGE UNIT20¥ IMAGE¥051121¥ IMAGE P |
| No.1003 | 2005/11/24 | Kobayashi Daigo | 50 | MALE | PLAIN RADIOGRAPHY | CRURAL AREA | Tsuboi | EXAMINATION | NO FINDINGS | STORAGE UNIT20¥ IMAGE¥051122¥ IMAGE P |
| No.1004 | 2005/12/2 | Tanaka Tatsuya | 53 | MALE | PLAIN RADIOGRAPHY | CRURAL AREA | Tsuboi | POST- SURGERY CHECK | LEFT FEMORAL FRACTURE | STORAGE UNIT20¥ IMAGE¥051123¥ IMAGE P |

FIG. 11

| | 31a | 31b | 31c | 31d | 31e | 31f | 31g | 31h | 31j | 31k | 31m |
|---|---|---|---|---|---|---|---|---|---|---|---|
| | REPORT NUMBER | EXAMINATION DATE | PATIENT NAME | AGE | SEX | EXAMINATION TYPE | IMAGED-SITE | DOCTOR | EXAMINATION PURPOSE | ESTABLISHED -DISEASE -NAME | STORAGE- LOCATION |
| | No.1003 | 2005/11/24 | D.K | 50 | MALE | PLAIN RADIOGRAPHY | CRURAL AREA | Tsuboi | EXAMINATION | NO FINDINGS | STORAGE UNIT20¥ IMAGE¥051120¥ IMAGE P |
| | No.10051 | 2006/03/21 | S.M | 50 | MALE | PLAIN RADIOGRAPHY | CRURAL AREA | Tsuboi | EXAMINATION | NO FINDINGS | STORAGE UNIT20¥ IMAGE¥060321¥ IMAGE P |
| | No.10082 | 2006/07/11 | T.M | 50 | MALE | PLAIN RADIOGRAPHY | CRURAL AREA | Yamashita | EXAMINATION | NO FINDINGS | STORAGE UNIT¥ IMAGE¥060711¥ IMAGE P |

FIG. 12

| 31a | 31b | 31c | 31d | 31e | 31f | 31g | 31h | 31j | 31k | 31m |
|---|---|---|---|---|---|---|---|---|---|---|
| REPORT NUMBER | EXAMINATION DATE | PATIENT NAME | AGE | SEX | EXAMINATION TYPE | IMAGED SITE | DOCTOR | EXAMINATION PURPOSE | ESTABLISHED-DISEASE-NAME | STORAGE-LOCATION |
| No.1004 | 2005/12/2 | T.T | 55 | FEMALE | PLAIN RADIOGRAPHY | CRURAL AREA | Tsuboi | POST-SURGERY CHECK | LEFT FEMORAL FRACTURE | STORAGE UNIT 20¥ IMAGE¥051120¥ IMAGE P |
| No.1031 | 2005/12/24 | S.M | 53 | MALE | PLAIN RADIOGRAPHY | CRURAL AREA | Tsuboi | POST-SURGERY CHECK | LEFT FEMORAL FRACTURE | STORAGE UNIT 20¥ IMAGE¥051224¥ IMAGE P |

IMAGE-DISPLAY DEVICE AND AN IMAGE-DISPLAY SYSTEM

BACKGROUND OF THE INVENTION

1. Field of the Invention

The present invention relates to the art of displaying a medical image.

2. Description of the Related Art

In recent years, in accordance with the development of digitization and networking in hospitals, medical images obtained for image examination have been increasingly managed in a filmless method. The obtained medical images are stored in a digital data format and provided as needed to an image-display device through a network and a portable storage media.

The medical image is image information for a subject, and is obtained by an imaging diagnostic system. Examples of imaging diagnostic systems include: an ultrasonic diagnostic device that transmits/receives ultrasound to the subject in order to observe the inside of a subject; an X-ray CT (Computed Tomography) that exposes X-rays to the subject and then obtains the transmitted X-rays in order to observe the inside of the subject; an MRI (Magnetic Resonance Imaging) device that generates magnetic fields and electromagnetic waves and then receives electrical waves generated from, for example, the hydrogen nuclei of the inside of the subject, in order to observe the inside of the subject; and a nuclear medicine diagnosis device (a SPECT device and a PET device) that detects gamma rays radiated from radioisotopes that have been administrated to the inside of the subject, in order to observe the inside of the subject. The medical images obtained by theses imaging diagnostic system are used for radiogram interpretations, conferences, and informed consent.

For a radiogram interpretation, the medical image is transmitted through a network to the image-display device that has a function supporting report preparation, and a report is prepared while the medical image is displayed in the image-display device. The report is a document that describes findings based on the radiogram interpretation of the medical image. Additionally, for conferences and informed consent, the medical image is transmitted to the image-display device through a network, and decisions on treatment course are displayed along with explanations for the patient about their medical condition, symptoms, and future treatment options.

However, for third parties who view the medical images at a conference or at an informed consent, and in particular for patients who have poor medical knowledge, they may view their own medical images without understanding where the affected site is, how severe the medical conditions and symptoms for that affected site are, and what the difference is compared to an able-bodied person, and therefore, even in the case of receiving informed consent, anxiety regarding issues such as whether there are other treatment methods or not increases, and thus there is even the possibility that they may come to mistrust the doctor. Even when receiving an explanation about the treatment method, they cannot completely grasp what happens post-surgery, and thus the anxiety increases in this way as well, which results in the possibility that any mistrust they have towards their doctor is increased. As used hereinafter, an able-bodied person means a person who has no abnormalities within the range of the observed site that has been captured in the medical image.

By the way, in radiogram-interpretation operations, other medical images related to the medical image intended for the radiogram interpretation, particularly past images for the same patient, are often referred to. Past images showing other cases for the same site are also referred to at times. The findings are described by comparing the past images with the medical image intended for the radiogram interpretation. Therefore, a medical information system has been proposed for searching past medical images related to the medical image intended for the radiogram interpretation and then providing them to the image-display device (for an example, refer to Japanese Unexamined Patent Application Publication No. 2002-63280). This medical information system operates to register medical images in a case database, and to search similar cases that have been registered in this case database and the medical images related to the past information of the patient so that they can be displayed in the image-display device. The case database is compiled as a database of information on the findings and the image conditions, and used for searching the medical images for cases that are necessary for reference by, for example, a keyword search.

Such medical information systems have conventionally been directed toward use in referring, at the time of the radiogram-interpretation operations, to established diagnoses for identical past cases, but not directed toward use in conferences and informed consent. Therefore, while it has been possible to search for similar past cases, it has been difficult to search for and display medical images that are not recognized as similar cases, such as medical images of able-bodied persons who have no disease and/or injury or medical images obtained after surgery. As used herein, an established diagnosis means that the presence of a disease and/or injury has been proven. In other words, even though medical images are accumulated on a daily basis, they have not been utilized in any satisfactory way for conferences and informed consent.

SUMMARY OF THE INVENTION

The present invention has been developed in consideration of the abovementioned circumstances and the objective thereof is to provide art for obtaining, from an enormous quantity of medical-image groups, medical images of able-bodied persons and of post-surgery conditions, and for simultaneously displaying these medical images of able-bodied persons and of post-surgery conditions along with the patient's own medical image.

An image-display device according to the first embodiment of the present invention for solving the abovementioned problems is connected with an image-storage device configured to store medical images and a report-storage device configured to accumulate radiogram-interpretation reports for said medical images, so as to allow for data communication. The radiogram-interpretation reports that have been accumulated in the report-storage device include a database in which information on the characteristics of a medical image corresponding to the radiogram-interpretation report is associated with information for identifying the medical image. This image-display device comprises: a display unit configured to display a patient's medical image; and a searching unit configured to search said database based on information on the characteristics of the said patient's medical image, and identifying a related medical image.

Additionally, an image-display system according to the second embodiment of the present invention comprises: an image-storage device configured to store medical images; a report-storage device configured to accumulate radiogram-interpretation reports for the said medical image, wherein the said radiogram-interpretation report includes a database in which the information on the characteristics of a medical image corresponding to the radiogram-interpretation report is associated with information for identifying the medical image; a display unit configured to display a patient's medical image; and a searching unit configured to search said database based on information on the characteristics of the said patient's medical image, and identifying an associated medical image.

The abovementioned first or second embodiment makes it possible to search for a medical image that may be intended for comparison with a patient's medical image by simply compiling the contents of the reports as a database, and thus it can prevents the need for a system operator to perform the operations of selecting the medical images of able-bodied persons and post-surgery conditions and displaying them on the database, resulting in excellent convenience.

Additionally, the third embodiment of the present invention stores, in a database, information with the names of established diseases, which includes cases with no findings, or information identifying post-surgery images. The image-display device identifies associated medical images based on the information on established-disease name showing cases with no findings or the post-surgery-image-identifying information.

This makes it possible to obtain the medical images of able-bodied persons and to display them in comparison with the patient's medical image, and therefore third parties who view the medical images, particularly patients who have poor medical knowledge, can easily understand where the affected site is, how severe the medical conditions and symptoms for that affected site are, and what the difference is from able-bodied persons, which results in the effectiveness of informed consent and conferences. Alternatively, this makes it possible to obtain the post-surgery medical images and to display them in comparison with the patient's medical image, and therefore the third parties who view the medical images, particularly patients who have poor medical knowledge, can easily understand how surgery will be performed and how they will recover, which results in the effectiveness of informed consent and conferences.

Furthermore, the fourth embodiment of the present invention predetermines a preference order and an information range for information on the characteristics of a patient's medical image. If associated medical images are not found as a result of searching the said database, a search will be performed again by expanding the search range according to the preference order and the information range, which have been predetermined.

This makes it possible to obtain medical images of able-bodied persons or of post-surgery conditions that have the same or similar characteristics as the patient's medical image, except for the existence/nonexistence of the affected site and the differences between pre-surgery and post-surgery, and thus it is easy to compare them with the patient's medical image, resulting in further effectiveness in informed consent and conferences.

BRIEF DESCRIPTION OF THE DRAWINGS

FIG. 2 is a pattern diagram illustrating a display screen of an image-display device.

FIG. 5 is a pattern diagram illustrating the contents of a report database.

FIG. 11 is a diagram illustrating a corresponding list related to medical images of able-bodied persons that is displayed by searching a report database.

FIG. 12 is a diagram illustrating a corresponding list related to medical images of post-surgery conditions that is displayed by searching a report database.

DETAILED DESCRIPTION OF THE EMBODIMENT

The preferred embodiments for an image-display system and an image-display device according to the present invention will be described below in details with reference to drawings.

Figure 1:
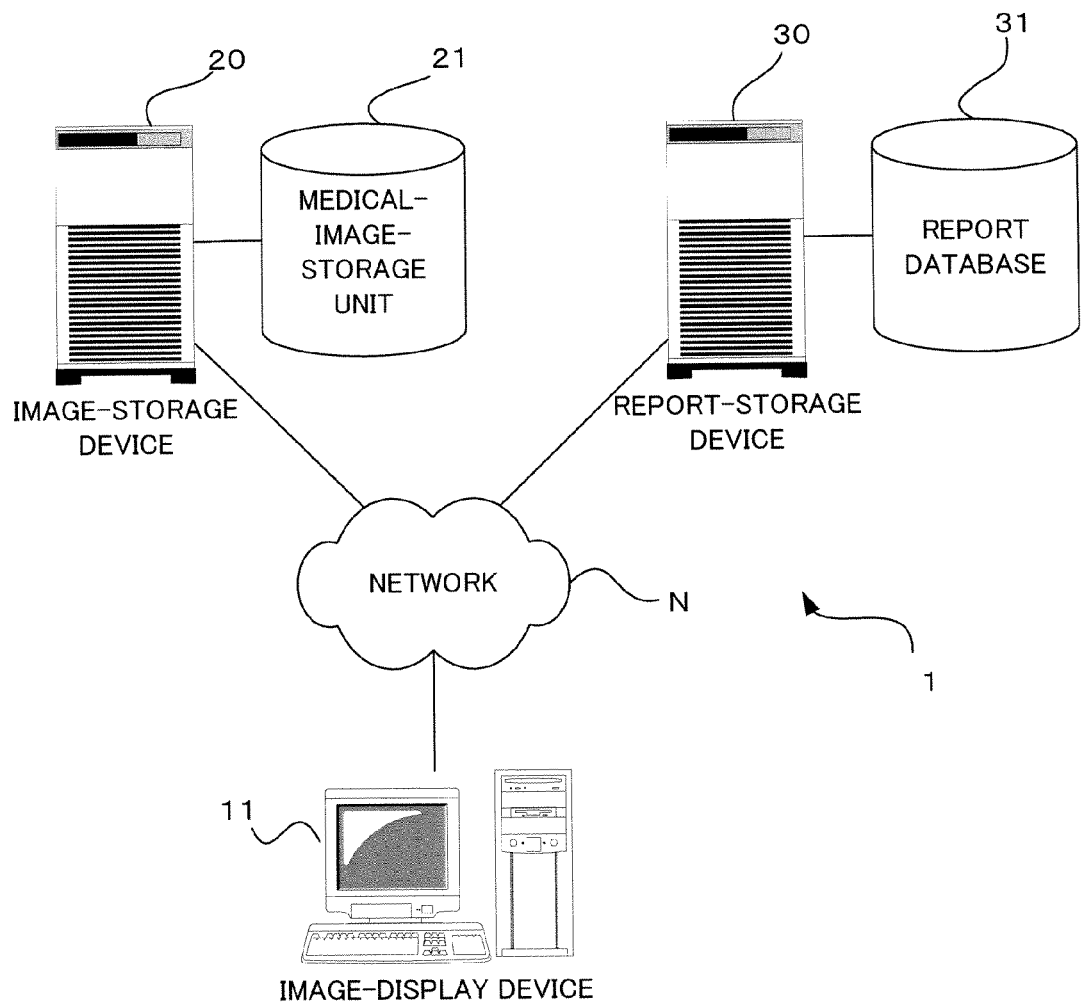
FIG. 1 is a block diagram illustrating a network configuration for an image-display system.

FIG. 1 illustrates an entire configuration for an image-display system. The image-display system 1 is a system for storing medical images and searching and displaying medical images that correspond to specified conditions. The image-display system 1 of the present embodiment obtains and displays, based on a search condition including the contents of reports prepared by an interpreting doctor, medical images that are radiogram-interpretation sources for the reports corresponding to the search condition.

In particular, this image-display system 1 searches the reports that have the contents of able-bodied persons' image-identifying information or post-surgery-image identifying information, and then obtains and displays medical images of able-bodied persons or of post surgery conditions that are radiogram-interpretation sources for those reports. The able-bodied persons' identifying information is identification information showing the medical images of able-bodied persons. The post-surgery-image identifying information is identification information showing medical images of post-surgery conditions. In addition, this image-display system 1 obtains the medical images of able-bodied persons or of post-surgery conditions that have the same or similar characteristics as the patient's medical image except for the existence/nonexistence of the affected site and the differences between pre-surgery and post-surgery, and then simultaneously displays them with the patient's medical image. In other words, medical images related to the patient's medical image are identified and obtained. This is preferable for use at conferences and informed consent for explaining medical conditions and symptoms to patients that have poor medical knowledge. Same or similar characteristics means that the characteristics for the medical image, such as the patient's age, sex, examination type, and imaged (radiographed) site, are the same in all or any of them, or similar in any of them. It is preferable that the examination type and the imaged site intended for comparisons at conferences and informed consent are the same, but they may simply be similar depending on the cases. For example, when explaining post-surgery bolt-fixing, in some cases there may be no problem in explaining while making reference to a different fracture site.

This image-display system 1 comprises an image-display device 11 for displaying medical images, an image-storage device 20 for storing medical images, and a report-storage device 30 for storing radiogram-interpretation reports by compiling them as a database, each of which is connected on a network N and configured to allow for data communication.

The network N is an electrical communication line that is capable of transmitting electronic data, for example, a telephone line network, an ISDN, a FDDI, a leased line, a mobile communication, a communications satellite network, a CATV, or a LAN, or a combination thereof is employed. The image-display device 11, the image-storage device 20, and the report-storage device 30 perform transmission/receiving of data in conformity with a data-communication control standard, such as a WWW (World Wide Web), a TCO/IP protocol, or a DICOM (Digital Imaging and Communications in Medicine) protocol.

The image-storage device 20 comprises a medical-image-storage unit 21. The medical-image-storage unit 21 stores various medical images. The medical-image-storage unit 21 stores, as various kinds of medical images, medical images for various patients, medical images for various sites, medical images obtained for examinations or checks of post-surgery courses, medical images obtained by capturing using various capturing methods, medical images for which established disease names can actually be obtained, or medical images for which no problems have been found. An established disease name means a disease name that has been obtained by an established diagnosis. The medical-image-storage unit 21 indexes storage areas for each medical image, for example in a tree structure, and therefore each medical image is clearly defined to an arbitrary storage location. The image-storage device 20 retrieves the medical images stored in the storage area that is indicated by storage-location information received through the network N, and then transmits, through the network N, the medical images to the source that transmitted the storage-location information.

The report-storage device 30 accumulates radiogram-interpretation reports and comprises a report database 31 for these radiogram-interpretation reports. The report database 31 stores the reports by compiling the contents thereof as a database. The reports describe information that identifies the medical images intended for radiogram interpretation. Examples of this information that identifies medical images include storage location, which is information showing a storage-location address for the medical image located within the image-storage device 20. The report-storage device 30 searches the reports that meet all the search conditions received through the network N. Once the corresponding report is found, the storage-location information for the medical image intended for radiogram interpretation of the corresponding report is transmitted to the transmission source of the search conditions through the network.

The image-display device 11 obtains and displays the medical images from the image-storage device 20. The storage-location information for the medical images is transmitted to the image-storage device 20, and the medical images stored in the storage area that is shown by said storage-location information are obtained. The storage-location information is obtained from the report-storage device 30. The image-display device 11 transmits the search conditions to the report-storage device 30, and then receives the storage-location information for the medical images intended for radiogram interpretation of the reports corresponding to said search conditions. This image-display device 11 transmits, to the report-storage device 30, the search conditions by adding the able-bodied-persons-image-identifying information or the post-surgery-image-identifying information, therefore obtains the storage-location information for the medical images of able-bodied persons or of post-surgery conditions, and obtains the medical images of able-bodied persons or of post-surgery conditions which have been stored in said storage location. Additionally, the information showing the characteristics of the patient's medical image is transmitted as a search condition, and therefore the medical images of able-bodied persons or of post-surgery conditions, which have the same or similar characteristics as the patient's medical image except for the existence/nonexistence of the affected site and the differences between pre-surgery and post-surgery, are obtained.

FIG. 2 is a pattern diagram illustrating a display screen of this image-display device 11. The image-display device 11 comprises two monitors: a doctor-sided monitor 110 and a patient-sided monitor 111. The doctor-sided monitor 110 is a monitor that is viewed only by a doctor when having discussions with a patient. The patient-sided monitor 111 is a monitor that is viewed by both the doctor and the patient for the explaining information to the patient. The doctor-sided monitor 110 is provided with a report-display area 112. The report-display area 112 displays for a patient receiving the explanation reports prepared through medical-image interpretation. The image-display device 11 extracts the information showing the characteristics of the patient's medical image from the report displayed on this report-display area 112, and then transmits it to the report-storage device 30 as a search condition by adding the able-bodied persons' image-identifying information or post-surgery-image-identifying information. The patient-sided monitor 111 is divided into a display are for the patient's medical image 113 and a display area for medical images of able-bodied persons or of post-surgery conditions 114. The display area for the patient's medical image 113 displays the medical image of the patient receiving the explanation. The display area for medical images of able-bodied persons or for post-surgery conditions 114 displays medical images of able-bodied persons or of post-surgery conditions that are the same as or similar to the patient's medical image except for the existence/nonexistence of the affected site and the difference between pre-surgery and post-surgery. Since the patient's medical image and the medical image of able-bodied persons or of post-surgery conditions are displayed simultaneously, even patients who have poor medical knowledge can understand where the affected site is, how severe their own medical condition and symptoms are, and what the difference is from able-bodied persons, increasing the significance of the informed consent.

Figure 3:
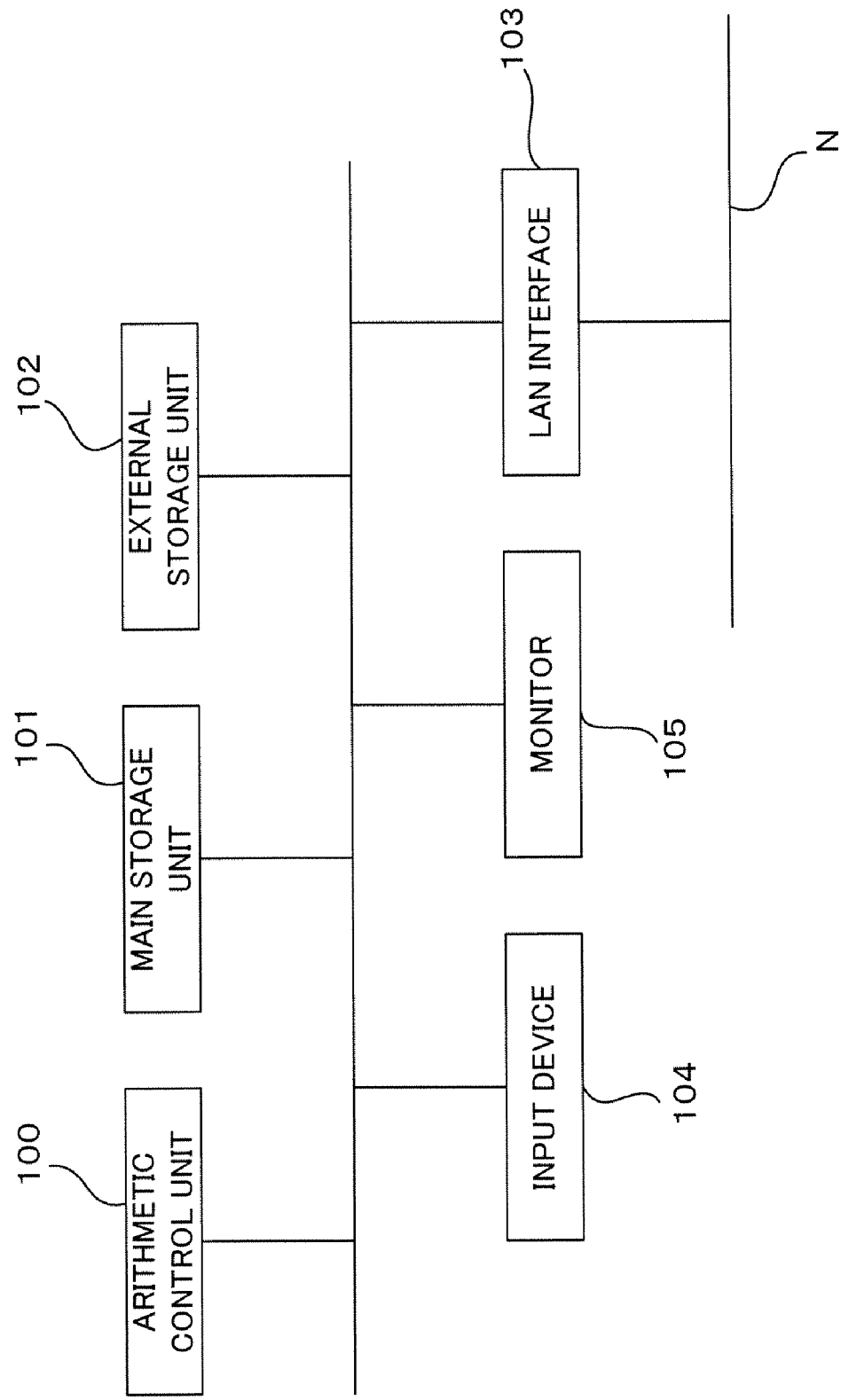
FIG. 3 is a block diagram illustrating a hardware configuration for each device comprised in an image-display system.

FIG. 3 is a block diagram illustrating a hardware configuration of the image-display device 11, the image-storage device 20, and the report-storage device 30. They form the said image-display system 1. The image-display device 11, the image-storage device 20, and the report-storage device 30 are configured with a computer. Each of them internally comprises an arithmetic control unit 100 (CPU: Central Processing Unit and a graphic chip), a main storage unit 101 (RAM: Random Access Memory), an external storage unit 102 (HDD: Hard Disk Drive), and a LAN (Local Area Network) interface 103, which are connected with a common line to allow for mutual data input/output.

The arithmetic control unit 100 decodes and executes programs to calculate data and control a device. The main storage unit 101 is a work area for the arithmetic control unit, and temporarily stores a part of data retrieved by developing the programs. The external storage unit 102 stores OS (operating system) and each of the programs used for displaying images. The LAN interface 103 connects directly to the network N and mediates data communication. Additionally, the image-display device 11 comprises a monitor 105 for displaying images and an input device 104 for receiving commands inputted by an operator. The monitor 105 is comprised of an LCD (Liquid Crystal Display) display or a CRT (Cathode Ray Tube) display, and displays medical images, radiogram-interpretation reports, and a GUI (Graphical User Interface) for displaying them, according to drawing data that have been outputted by the arithmetic control unit 100. The input device 104 is a keyboard and a mouse that has a wheel-tracking function and the like, and outputs signals to the arithmetic control unit 100 according to the operation performed by the operators. The monitor 105 comprises two monitors: a doctor-sided monitor 110 and a patient-sided monitor 111.

Figure 4:
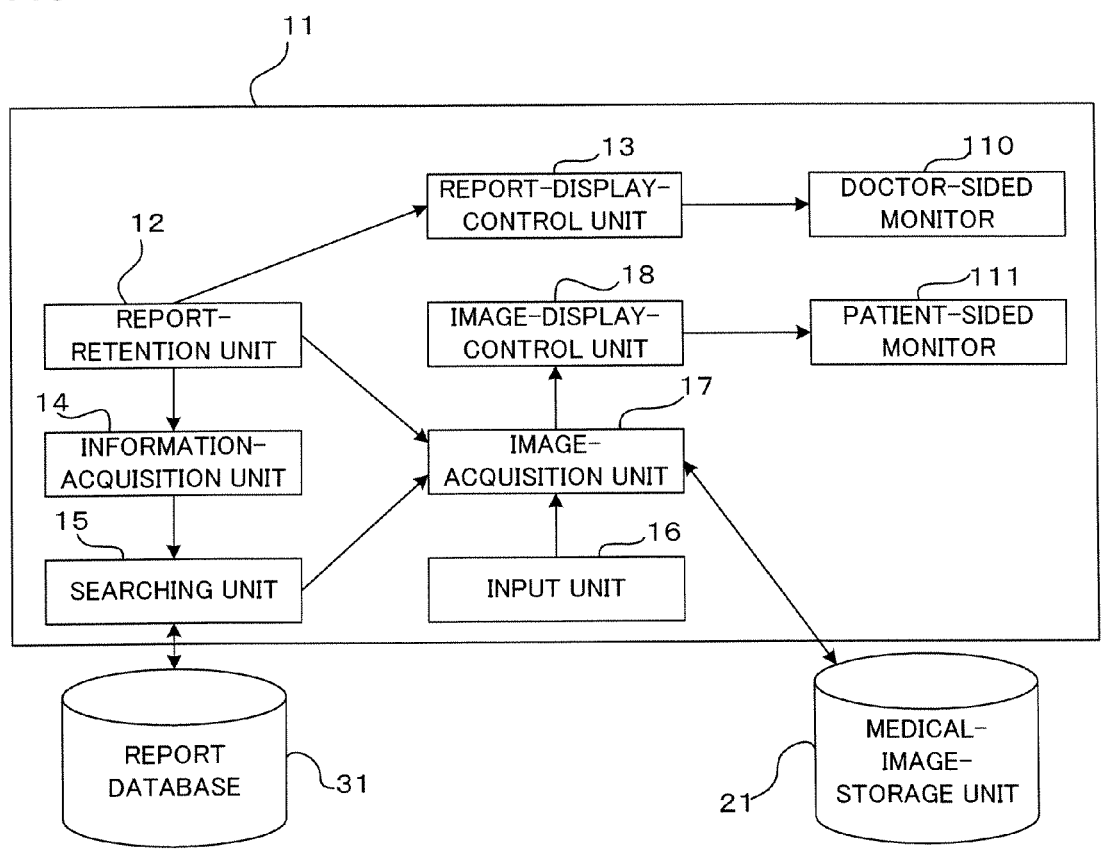
FIG. 4 is a block diagram illustrating a functional configuration for an image-display device.

FIG. 4 illustrates a configuration realized by executing programs that are stored in the image-display device 11 that have such hardware configuration. The image-display device 11 comprises a report-retention unit 12 and a report-display-control unit 13 as a means for displaying reports. An information-acquisition unit 14 and a searching unit 15 are comprised as a means for obtaining the storage-location information. An image-acquisition unit 17 and an image-display-control unit 18 are comprised as a means for displaying a patient's medical image and a medical image of able-bodied persons or of post-surgery conditions. Additionally, an input unit 16 for receiving inputs from operators is also included.

The report-retention unit 12 comprises devices for storing data, such as the external storage unit 102 and the main storage unit 101. This report-retention unit 12 stores patient reports. The data of the reports include the report information. These patient reports are received through the network N from the report-storage device 30 and stored in the report-retention unit 12. The report information is data extracted from character strings and the tag areas in the contents of the report, and includes characteristics of the medical image of patients that have been interpreted. This report information includes information showing the report number, examination date, the patient's name, age, sex, and examination type, the imaged site, the doctor responsible, the examination's purpose, the established disease name, and the storage location. Out of these, the characteristics of the medical image of a patient are age, sex, examination type, imaged site, doctor responsible, examination purpose, and established disease name.

The report-display-control unit 13 comprises the arithmetic control unit 100. The report-display-control unit 13 retrieves the patient reports from the report-retention unit 12, extracts the report information, and then causes the doctor-sided monitor 110 to display the reports and the report information separately.

The information-acquisition unit 14 comprises the arithmetic control unit 100. The report information is retrieved from the data of the reports stored in the report-retention unit 12, and the characteristics of the patient's medical image, which has been a source for radiogram interpretation, are extracted. The extracted characteristics of the medical image are the age and a sex of a patient, and the examination type and the imaged site for which the medical image have been obtained. In other words, in order to obtain the medical images of able-bodied persons or of post-surgery conditions that have the same or similar characteristics with the patients' medical images, such as age, sex, examination type and imaged site for which the medical images have been obtained, information on these characteristics is extracted from the report information for patients.

The searching unit 15 comprises the arithmetic control unit 100 and the LAN interface 103. This searching unit 15 generates the searching condition for an AND search, which includes characteristics information obtained by the information-acquisition unit 14 and the information identifying images of able-bodied persons or post-surgery conditions, and then transmits them to the report-storage device 30 together with searching commands by using a structured query language that constructs a database search such as DISCOM Q/R (Query and Retrieve) or SQL. The searching unit 15 generates the search conditions, including the information identifying the images of able-bodied persons or post-surgery conditions in accordance with the inputs performed by operators using the input unit 16. The characteristics information is a search key for searching medical images that are the same as or similar to the patient's medical image, and the information identifying images of able-bodied persons is a key for searching the medical images for able-bodied persons, and the information identifying images of post-surgery conditions is a key for searching the medical images. This searching unit 15 predetermines a preference order and an information range depending on the types of the characteristics information. This preference order and the information range are predetermined so that the medical images of able-bodied persons or post-surgery conditions that preferably have the same characteristics as the patient's medical image can be searched. First, the characteristics information is transmitted to the report-storage device 30 based on the searching condition showing a perfect match, but if there is no corresponding medical image, the condition will be deleted or relaxed in order from lowest priority. The information showing the imaged site and the examination type are placed as high priority. The age is relaxed within the specified range. The sex is set as a low priority.

The image-acquisition unit 17 comprises the arithmetic control unit 100 and the LAN interface 103. This image-acquisition unit 17 accesses the image-storage device 20 shown by the storage-location information that has been obtained from the report-storage device 30, and then causes the medical images that are stored in the storage area shown by the storage-location information to be transmitted through the network N. Once the medical images corresponding to the search conditions generated in the searching unit 15 are found, the corresponding list for the medical images is transmitted from the report-storage device 30 to the image-display device 11 through the network N. The list for the medical images is displayed on the doctor-sided monitor 110. Once the desired medical image is selected by the operator using the input unit 16, the image-acquisition unit 17 obtains the storage-location information for the selected medical images of able-bodied persons or of post-surgery conditions. This storage-location information is included in the list and transmitted through the network N. Additionally, the storage-location information, such as a hyperlink, described in the patient reports is obtained, and then the patient's medical images stored in the storage area shown by said storage-location information are obtained through the network N.

The image-display-control unit 18 comprises the arithmetic control unit 100. This image-display-control unit 18 simultaneously displays the patient's medical image and the medical image for able-bodied persons or for post-surgery conditions that have been obtained by the image-acquisition unit 17 on the patient-sided monitor 111.

FIG. 5 is a pattern diagram illustrating the report database 31 comprised in the report-storage device 30. The report database 31 is created from the report information included in the reports. The report database 31 is created by extracting the characteristics information showing the characteristics of the medical image from the report information included in the reports, separating this characteristics information into various data items, and compiling them as a table. The report database 31 includes data items such as report-number information 31a, examination-date information 31b, patient-name information 31c, age information 31d, sex information 31e, examination-type information 31f, imaged-site information 31g, information about the doctor responsible 31h, examination-purpose information 31j, established-disease-name information 31k, and storage-location information 31m. These characteristics information are extracted from the report information and compiled as a table. The patient-name information 31c, the age information 31d, the sex information 31e, the examination-type information 31f, and the imaged-site information 31g are the same items as the characteristics information transmitted from the image-display device 11 as the ones showing the characteristics of the patient's medical image. This report database 31 stores the information identifying the medical images of able-bodied persons or of post-surgery conditions. Examination-purpose information 31j that indicates "post-surgery check" is equivalent to the post-surgery-image-identifying information. Established-disease-name information 31k that indicates "no findings" is equivalent to the able-bodied persons' identifying information. Reports describing "post-surgery check" as the examination-purpose information 31j are created by interpreting the medical images obtained for the post-surgery check. Reports describing "no findings" as the established-disease-name information 31k are created by interpreting the medical images obtained for able-bodied persons. The searching unit 15 includes, in the search condition, the established disease name showing "no findings" as the able-bodied persons' identifying information, and the examination purpose showing "post-surgery check" as the post-surgery-image-identifying information, and then transmits them to the report-storage device 30.

Figure 6:
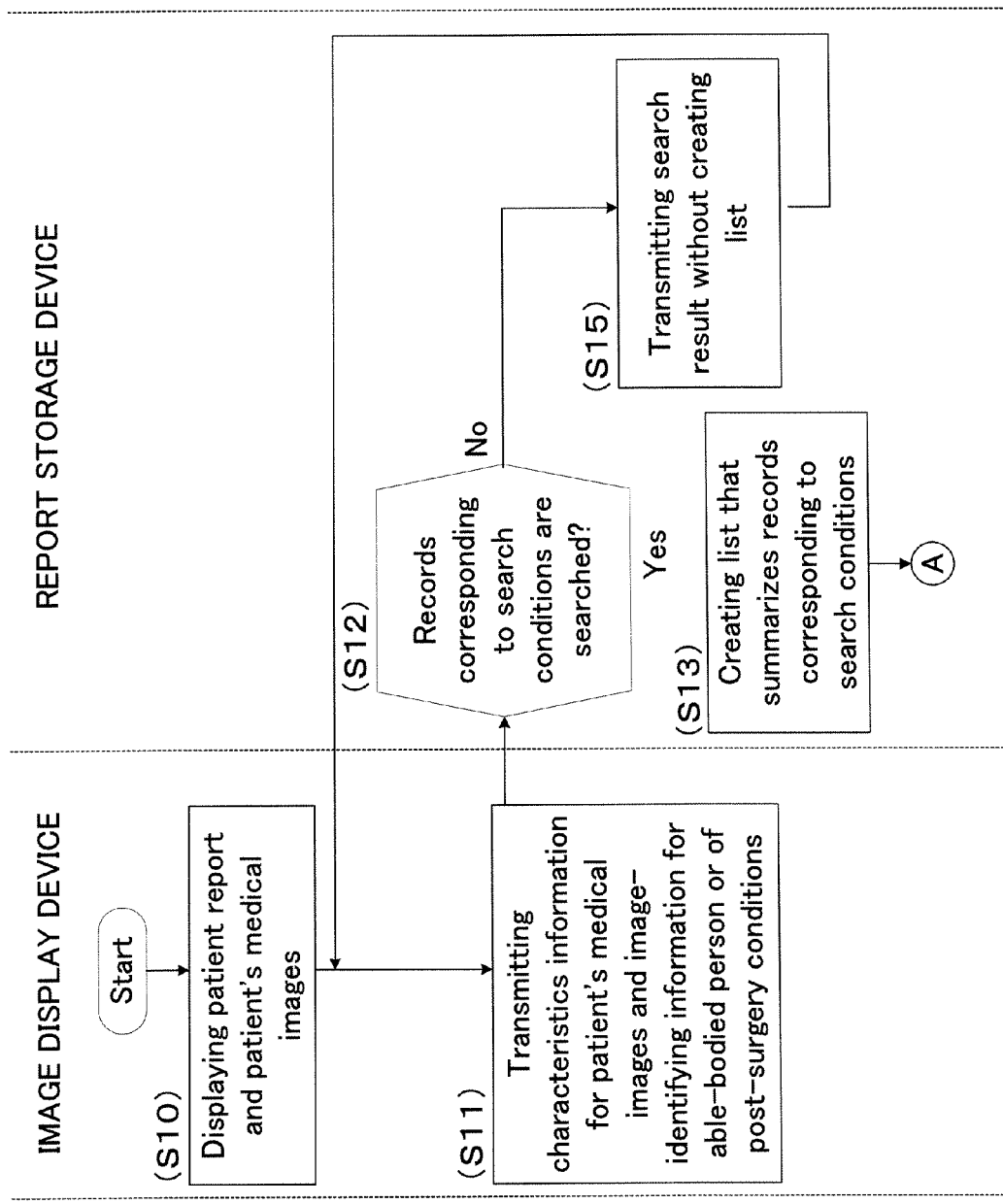
FIG. 6 is a flowchart illustrating an operation of an image-display system.
Figure 7:
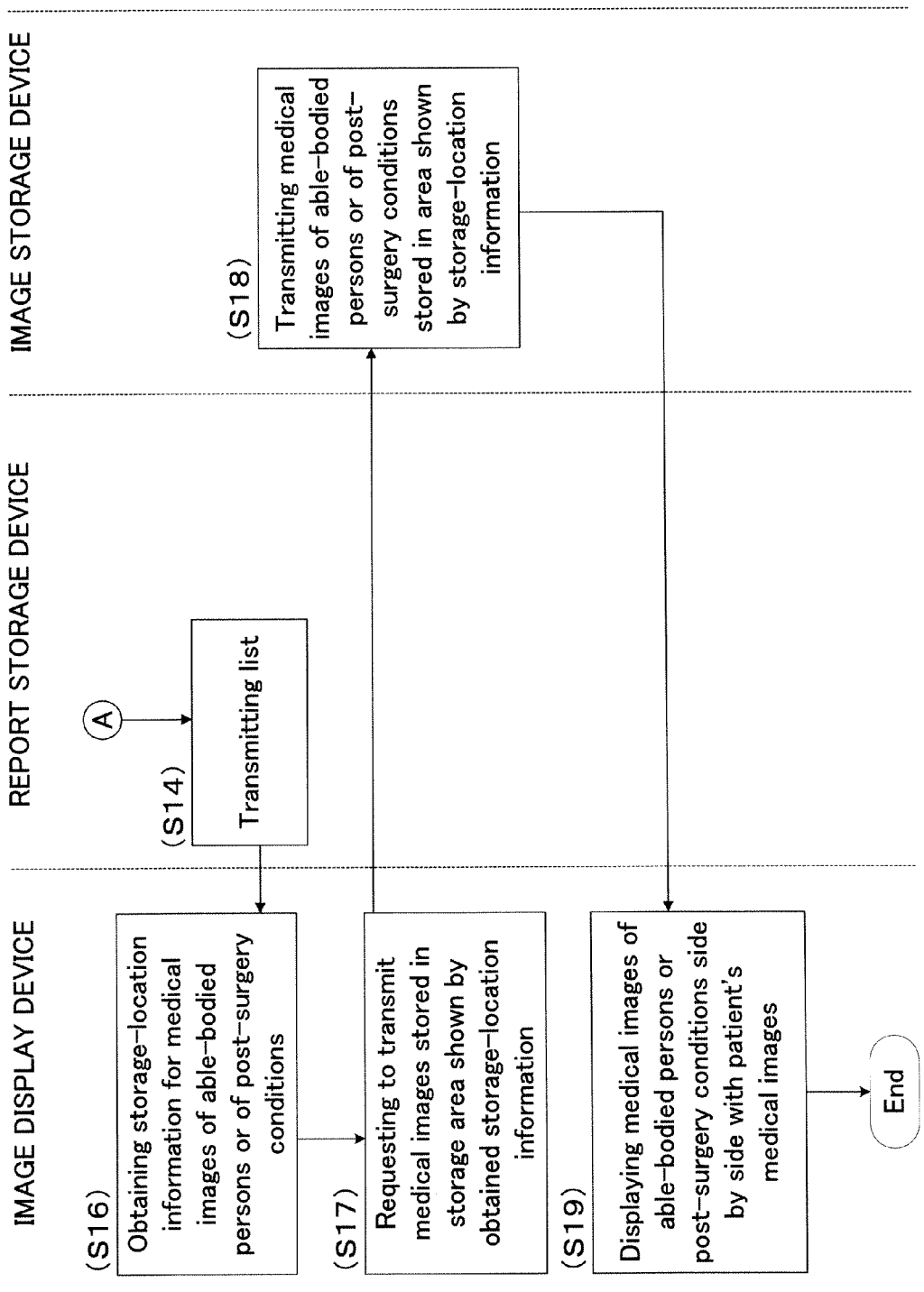
FIG. 7 is a flowchart illustrating an operation of an image-display system.

An operation for displaying an image according to such image-display system 1 is herein described. FIG. 6 and FIG. 7 are flowcharts according to an operation of the image-display system 1. First, the patient report and the patient's medical image are preliminarily displayed in the image-display device 11 (S10). The image display device 11 transmits to the report-storage device 30 the searching command based on the search conditions, including the characteristics information showing the characteristics of the patient's medical image obtained from patient reports as well as the able-bodied persons' image-identifying information or the post-surgery-image-identifying information (S11).

Once the search command is received by the report-storage device 30, records corresponding to the search condition are searched for from the report database 31 (S12). If there are records corresponding to the search condition (S12, Yes), a list that summarizes the records corresponding to said search conditions will be created (S13), and then the list will be transmitted to the image-display device 11 (S14). If there are no records corresponding to the search conditions (S12, No), the search result will be transmitted without the creation of the list (S15).

Once the list is received by the image-display device 11, the storage-location information for the medical images of able-bodied persons or of post-surgery conditions is obtained according to the request from the operator using the input unit 16 (S16). The image-display device 11 requests the image-storage device 20, shown by the storage-location information for the obtained medical images of able-bodied persons or of post-surgery conditions, to transmit the medical images stored in the storage area shown by the storage-location information (S17). Once the request for transmitting the medical images of able-bodied persons or of post-surgery conditions that have been stored in the storage area shown by the storage-location information are received, the image-storage device 20 transmits the medical images of able-bodied persons or of post-surgery conditions that have been stored in said storage area to the image-display device 11 (S18). Once the medical images of able-bodied persons or of post-surgery conditions are received, the medical image-display device 11 simultaneously displays the medical images of able-bodied persons or of post-surgery conditions side-by-side with the patient's medical image (S19).

Figure 8:
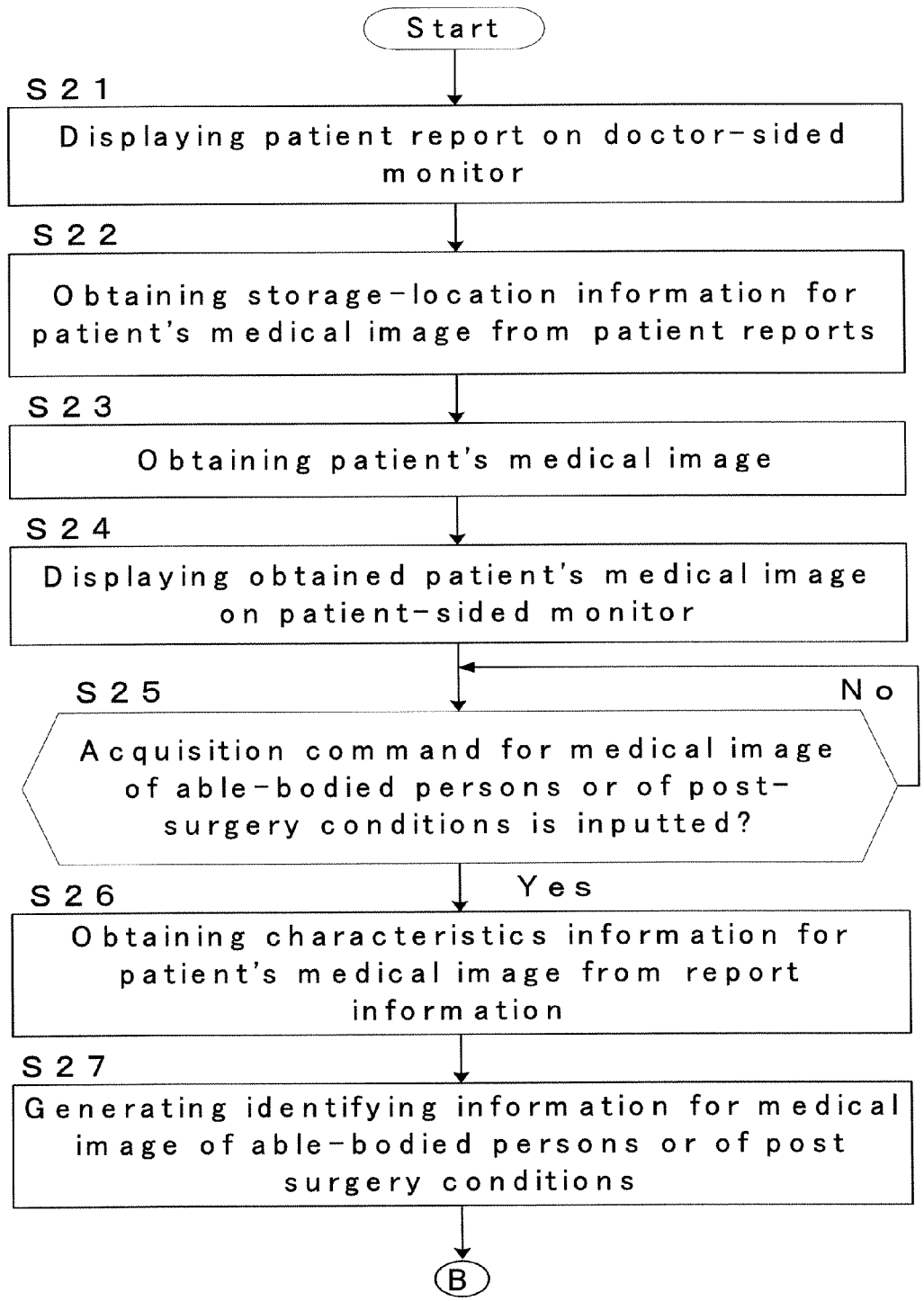
FIG. 8 is a flowchart illustrating an operation of an image-display device.
Figure 9:
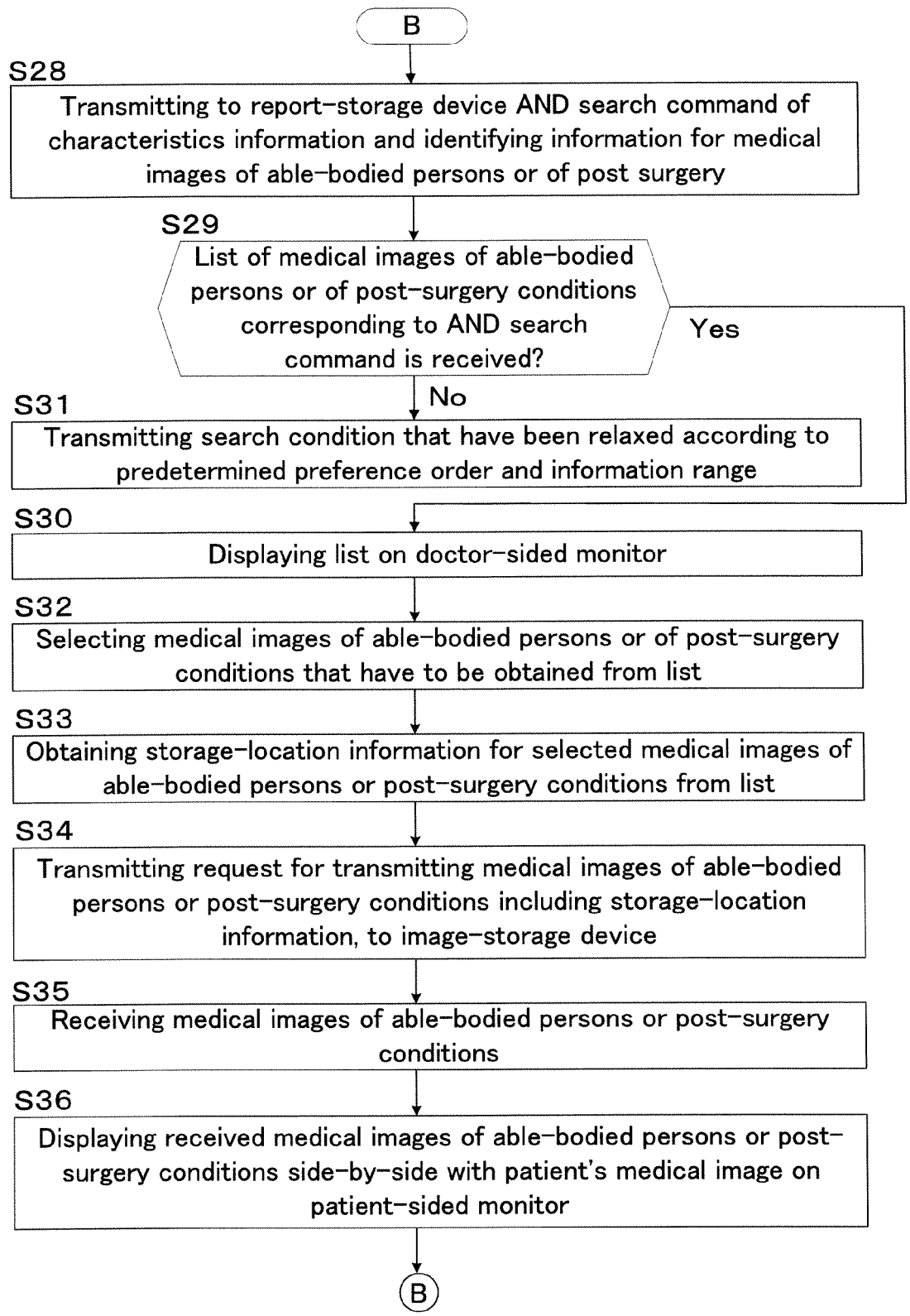
FIG. 9 is a flowchart illustrating an operation of an image-display device.

Furthermore, the detailed operations related to the operation for displaying the image according to the image-display device 11, are described. FIG. 8 and FIG. 9 are flowcharts illustrating details related to the operation for displaying the image of the image-display device 11. First, the report-display-control unit 13 causes the doctor-sided monitor 110 to display the patient report that was stored in the report-retention unit 12 (S21). The image-acquisition unit 17 obtains the storage-location information for the medical image intended for the radiogram interpretation from the patient reports that have been stored in the report-retention unit 12 (S22), and obtains the patient's medical image from the storage area corresponding to the storage-location information of the medical-image-storage unit 21 (S23). The image-display-control unit 18 causes the patient-sided monitor 111 to display the obtained patient's medical image (S24).

Once an acquisition command for the medical image of able-bodied persons or of post-surgery conditions is inputted using the input unit 16 (S25, Yes), the information-acquisition unit 14 obtains the characteristics information of the patient's medical image from the report information of the reports that are stored in the report-retention unit 12 (S26). Once the characteristics information is obtained, the searching unit 15 generates the able-bodied persons' identifying information or the post-surgery-image-identifying information according to the acquisition command (S27), and then transmits to the report-storage device 30 the searching command based on the search conditions for an AND search of the able-bodied persons' identifying information or the post-surgery-image-identifying information (S28). In cases where there are records corresponding to the search conditions in the report database 31, and the list of the medical images of able-bodied persons or of post-surgery conditions corresponding to the search condition is received from the report-storage device 30 (S29, Yes), the list is displayed on the doctor-sided monitor 110 (S30). On the other hand, in cases where there are no records corresponding to the search conditions, and the search result thereof is transmitted from the report-storage device 30 (S29, No), the searching unit 15 repeats transmitting the search condition that have been relaxed according to the preference order and the information range, which have been predetermined (S31).

Once the list is displayed on the doctor-sided monitor 110, and the operator selects the medical images of able-bodied persons or of post-surgery conditions that have to be obtained from the list by using the input unit 16 (S32), the image-acquisition unit 17 obtains the storage-location information for the selected medical images of able-bodied persons or post-surgery conditions from the list (S33). Once the storage-location information for the medical images of able-bodied persons or post-surgery conditions is received, the image-acquisition unit 17 transmits the request for transmitting the medical images of able-bodied persons or post-surgery conditions that have been stored in the storage area shown by the storage-location information, to the image-storage device 20 corresponding to said storage-location information (S34). Once the medical images of able-bodied persons or post-surgery conditions that have been stored in the storage area shown by the storage-location information are received from the image-storage device 20 (S35), the image-display-control unit 18 simultaneously causes the patient-sided monitor 111 to display the received medical images of able-bodied persons or post-surgery conditions side-by-side with the patient's medical image (S36).

Figure 10:
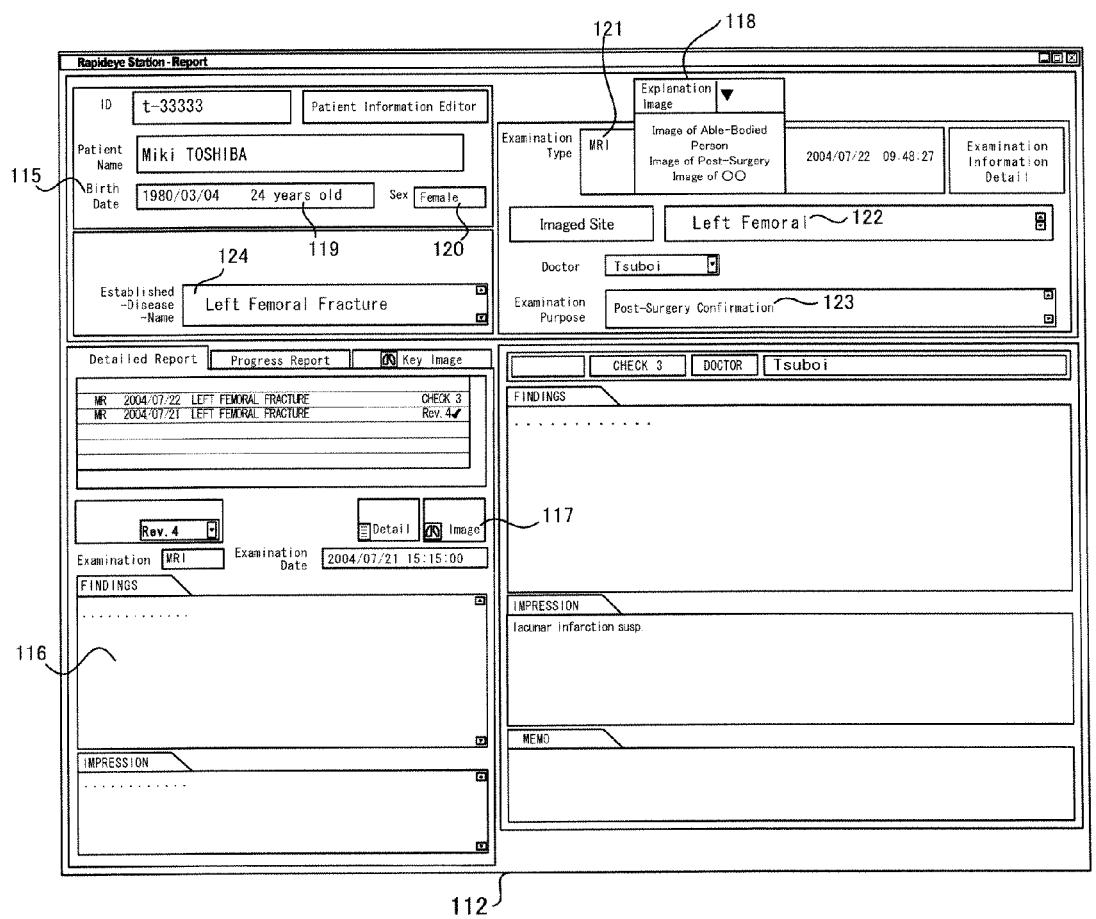
FIG. 10 is a pattern diagram illustrating a search screen for searching medical images of able-bodied persons or of post-surgery conditions.

FIG. 10 illustrates an example of a search screen for searching the medical images of able-bodied persons or of post-surgery conditions in said image-display system 1 and the image-display device 11. The doctor-sided monitor 110 displays a patient-report display screen 112. This patient-report display screen 112 contains the functions of the search screen. The patient-report display screen 112 is roughly divided into a report-information display area 115 and a patient-report display area 116. The report-information display area 115 displays the report information including the patient information; that is, the characteristics information of the medical images. As the report information, the patient's age is displayed in an age field 119, the patient's sex in a sex field 120, the examination type in an examination-type field 121, the imaged site in a imaged-site field 122, and an established disease name in an examination-purpose field 123 and an established-disease-name field 124. The displayed age, examination type by sex, imaged site, and examination purpose or an established disease name, are transmitted to the report-storage device 30 as the characteristics information of the medical image. Around these areas 115 and 116, icons are arranged for inputting each command. Examples of arranged icons include an image-display icon 117 for displaying, on a patient's medical-image display area 113 of the patient-sided monitor 111, the patient's medical image intended for the radiogram interpretation of the report displayed on the patient-report display area 116, and an explanation-image icon 118 for selecting the type of the medical images to be displayed on a display area of medical images of able-bodied persons or of post-surgery conditions 114 to be compared with the patient's medical image. The explanation-image icon 118 is, for example, a pull-down menu, which makes it possible to select the acquisition of the comparison image from the medical image of able-bodied persons or the medical image of post-surgery conditions. If the medical image of able-bodied persons is selected by this explanation-image icon 118, the able-bodied persons' identifying information as well as the established disease name showing "no findings" are included in the search conditions. If the medical image for post-surgery conditions is selected by this explanation-image icon 118, the post-surgery-image-identifying information as well as the examination purpose showing "post-surgery check" are included in the search conditions.

FIG. 11 illustrates the corresponding list of the medical images for able-bodied persons, which is received by the image-display device 11 as a result of searching the report database 31. The report-storage device 30 transmits the list of medical images of able-bodied persons or of post-surgery conditions that fit the search condition (that is, the able-bodied persons' identifying information or the post-surgery-image-identifying information), as well as the characteristics information of the patient's medical image. If the search condition is transmitted by including the able-bodied image identifying information, the list of the medical images of able-bodied persons, in which the established disease name information 31*k* shows "no findings" and which have the characteristics information of the patient's medical image, is transmitted. This list includes the storage-location information 31*m*.

For example, once the acquisition command for obtaining the medical images for "able-bodied persons" is pressed, the characteristics information is extracted from the patient report that has the report information in which the age is "50 years old", the sex is "male", the examination type is "plain radiography", and the imaged site is "crural area", which leads to the generation of the search conditions. Once the image-display device 11 transmits this search condition, the list of the medical images describing that the age is "50 years old", the sex is "male", the examination type is "plain radiography", the imaged site is "crural area", and the established disease name is "no findings", is transmitted to the image-display device 11. When this list is displayed on the doctor-sided monitor 110, the report-number information 31*a*, the examination-date information 31*b*, the patient-name information 31*c*, the age information 31*d*, the sex information 31*e*, the examination-type information 31*f*, the imaged site 31*g*, information on the doctor responsible 31*h*, the examination-purpose information 31*j*, the established-disease-name information 31*k*, and the storage-location information 31*m*, are all displayed, but the patient-name information 31*c* is initially displayed with the information hidden by an asterisk (*) or the like in order to protect personal information.

Additionally, when this list is displayed on the doctor-sided monitor 110, the doctor who conducted a log into the image-display device 11 is rearranged for displaying on the top, based on the information on the doctor responsible 31*h*. Records that have the same login ID and identical information on the doctor responsible 31*h* as the person who conducted the log-in are arranged on the top. By selecting an arbitrary record of the medical images from this list by means of the input unit 16, the storage-location information 31*m* included in said records is extracted.

FIG. 12 illustrates the corresponding list of the medical images for post-surgery conditions, which is transmitted by searching the report database 31. If the post-surgery-image-identifying information is included in the search conditions and sent, the list of the medical images for post-surgery is transmitted, in which the examination-purpose information 31*k* is "post-surgery check" and which have the characteristics information of the patient's medical image. If the medical images that have the characteristics information of the patient's medical image cannot be searched, in response to the receipt of the search result thereof, the search conditions are transmitted in which the preference order is provided and the information range is relaxed.

For example, once the acquisition command for obtaining the medical images for "post-surgery" is pressed, the characteristics information is extracted from the patient report that has the report information in which the age is "50 years old", the sex is "male", the examination type is "plain radiography", and the imaged site is "crural area", which leads to the generation of the search conditions. If there is no record corresponding to these search conditions, the search result thereof is returned from the report-storage device 30. The image-display device 11 provides the preference order and relaxes the information range, so that the age, for example, is provided as "50±5" and the condition of the patient's sex is not provided, and then transmits the search command. As a result of the abovementioned provided preference order and relaxed information range, a list of medical images in which the age is "55 years old" or "53 years old", the sex is "male" or "female", the examination type is "plain radiography", and the imaged site is "crural area", and the examination purpose is "post-surgery check", is transmitted to the image-display device 11. By selecting an arbitrary record of the medical images from this list by means of the input unit 16, the storage-location information 31m included in said records is extracted.

Figure 13:
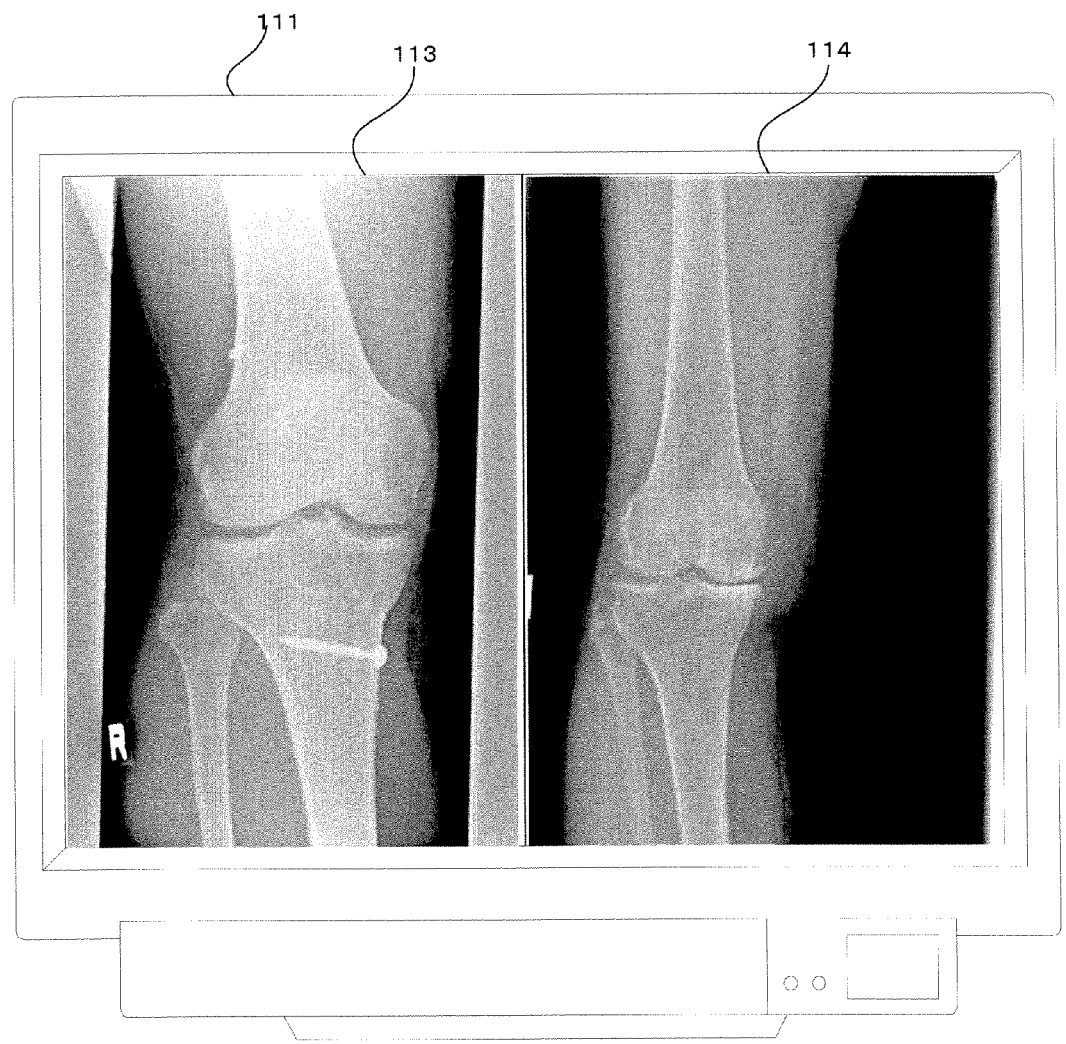
FIG. 13 is a pattern diagram illustrating a comparison screen, which is displayed by obtaining medical images of able-bodied persons.

FIG. 13 is a pattern diagram illustrating a comparison screen, which is displayed by obtaining medical images for able-bodied persons. The patient-sided monitor 111 is divided into a patient's medical-image display area 113 and an able-bodied person's medical-image display area 114, and the patient's medical-image display area 113 displays the patient's medical image and the able-bodied person's medical-image display area 114 displays the obtained medical images of able-bodied persons. For example, a medical image for a patient who has had a bolt inserted by surgery performed due to a right arm fracture, and a medical image of an able-bodied person who has no abnormalities such as a right arm fracture, are displayed. The patient can visually understand how the surgery has been performed by comparing the patient's medical image and the able-bodied person's medical image.

Figure 14:
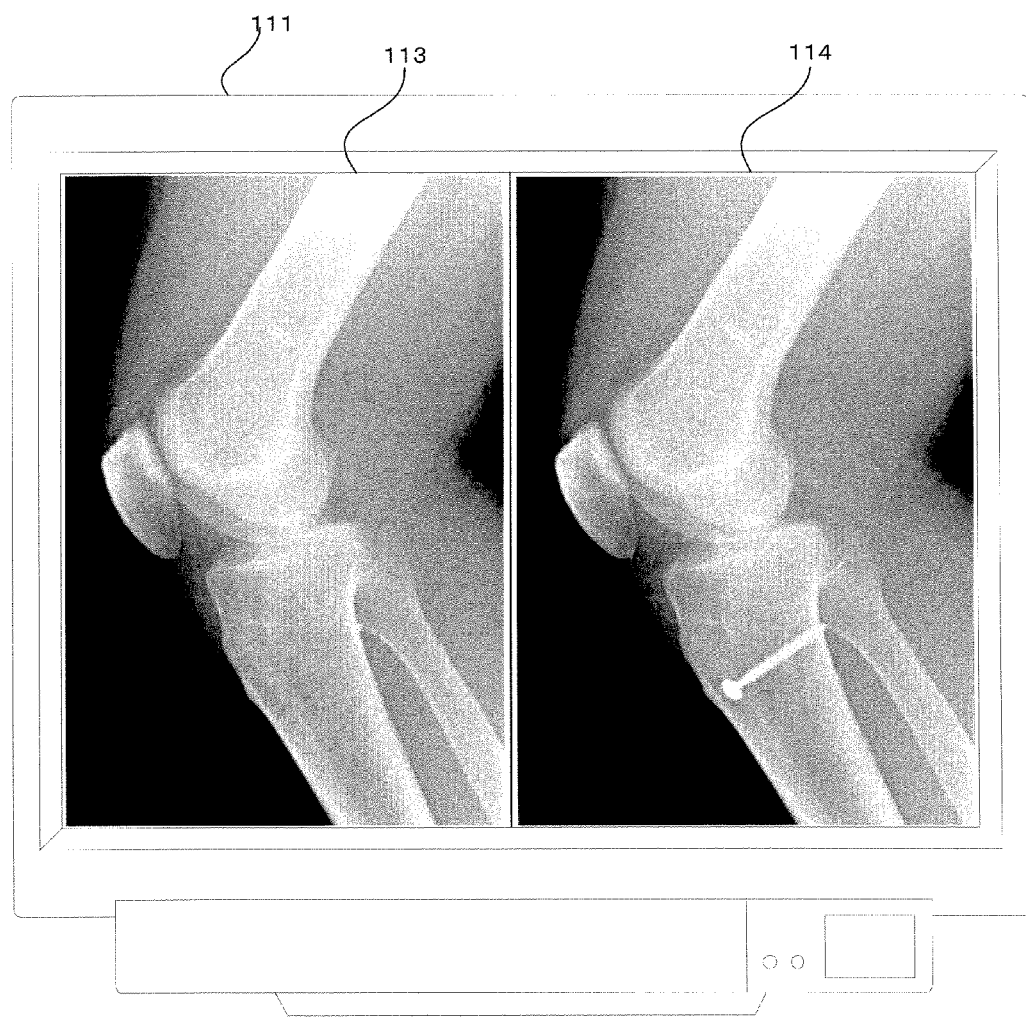
FIG. 14 is a pattern diagram illustrating a comparison screen, which is displayed by obtaining medical images of post-surgery conditions.

FIG. 14 is a pattern diagram illustrating a comparison screen, which is displayed by obtaining medical images for post-surgery conditions. The patient-sided monitor 111 is divided into a patient's medical-image display area 113 and a post-surgery medical-image display area 114, and the patient's medical-image display area 113 displays the patient's medical image and the post-surgery medical-image display area 114 displays the obtained medical images for post-surgery conditions. For example, a medical image for a patient who is injured with a femoral fracture and a medical image of post-surgery conditions in which a bolt has been surgically inserted for a femoral fracture are displayed. The patient can visually understand how the surgery will be performed by comparing the patient's medical image and the post-surgery medical image.

As described above, the present invention stores the storage-location information for the medical images and stores them as a database by pairing the storage-location information for the medical images of able-bodied persons or of post-surgery conditions with the able-bodied persons' image-identifying information or the post-surgery-image-identifying information, searches the storage-location information for the medical images for able-bodied persons and post-surgery from the database based on the able-bodied image-identifying information or the post-surgery-image-identifying information, and then simultaneously displays the medical image for able-bodied persons or for post-surgery conditions existing in the storage location and the patient's medical image. This makes it possible to obtain medical images of able-bodied persons or post-surgery conditions, and to display them in comparison with the patient's medical image, and therefore third parties who view the medical images, particularly patients who have poor medical knowledge, can easily understand where the affected site is, how severe the medical conditions and symptoms for said affected site are, and what the difference is from an able-bodied person, which increases the effectiveness of informed consent and conferences. It should be noted that persons who have poor medical knowledge include new persons such as interns, and can be trained by means of this image-display device 11 or image-display system 1. Additionally, it is beneficial for radiogram interpretation if the able-bodied persons' image and the post-surgery image are displayed for determining a disease, and it is possible that this image-display device 11 or the image-display system 1 can be used to assist radiogram interpretation.

Additionally, the database stores by pairing the storage-location information for the medical images with the imaged-site information, the examination-type information, and the information subject's age or sex for the medical images, and based on at least one or more of the imaged-site information, the examination-type information, the information subject's age or sex, for the patient's medical image that is to be displayed as well as the able-bodied image-identifying information or the post-surgery-image-identifying information, storage-location information of medical images of able-bodied persons or of post-surgery conditions that are the same as or similar to the patient's medical image may be searched. This makes it possible to obtain the medical images of able-bodied persons or of post-surgery conditions that have the same or similar characteristics as the patient's medical image except for the existence/nonexistence of the affected site and the differences between pre-surgery and post-surgery, and it is thus easier to compare them with the patient's medical image, which leads to further effectiveness in informed consent and conferences.

The database may be a database for reports including the examination-purpose information and the established-disease-name information that have been obtained by interpreting the medical images. The able-bodied persons' image-identifying information may be established-disease-name information that shows no findings, and the post-surgery identifying information may be examination-purpose information that shows a post-surgery check. This makes it possible to search the medical images of able-bodied persons or of post-surgery conditions by simply compiling, as a database, the report information described in the reports, and thus it can prevent a system operator from have to do the operations of selecting the medical images of able-bodied persons and post-surgery conditions and displaying them on the database, resulting in excellent convenience.

Additionally, the imaged-site information, the examination-type information, and the age or the sex for the patient's medical image, may be acquired from the reports obtained by interpreting the patient's medical image. This makes it possible to prevent the need for doctors who perform the conference and the informed consent to do the operations for inputting the search conditions, which leads to the achievement of automation as well as excellent convenience.

Additionally, in the present embodiment, the report database 31 is configured to extract the report information from the stored reports and to compile them as a table. Other than that, it may be configured to search by forming the report database 31 from the stored reports itself and directly retrieving the contents of the stored reports.

Furthermore, in the present embodiment, the able-bodied identifying information uses the established-disease-name information that shows no findings, and the post-surgery-image-identifying information uses examination-purpose information that shows a post-surgery check, but other codes that identify the able-bodied person and post-surgery conditions may be added in the report database 31.

What is claimed is:

1. An image-display device, which is connected so as to allow for data communication with an image-storage device configured to store medical images; and a report-storage device configured to accumulate radiogram-interpretation reports for said medical images, wherein said report-storage device includes a database in which, for each data item in the database, multiple items of characteristic information included in said radiogram-interpretation reports including established-disease name or examination purpose information are associated with information for identifying said medical images, the image-display device comprising:
- a display unit configured to display a patient's medical image; and
- a searching unit configured to search from said database a radiogram-interpretation report including at least one item of characteristic information which is the same as that of said patient's medical image and that indicates that established-disease-name information indicates that a subject of the searched radiogram-interpretation report is able-bodied or that said examination-purpose information is post-surgery to identify a medical image related to the searched radiogram-interpretation report in order to associate said identified medical image with said patient's medical image.

2. The image-display device according to claim 1, further comprising an image-acquisition unit configured to acquire associated medical images identified by said searching unit from said image-storage device,
- wherein said display unit simultaneously displays said medical image acquired by said image-acquisition unit and said patient's medical image.

3. The image-display device according to claim 1,
- wherein said database is a database for reports that include, in one of the items of characteristic information, established-disease-name information that includes those with no findings, and
- said searching unit searches said database, based on the characteristic information of said patient's medical image and established-disease-name information that indicates no findings.

4. The image-display device according to claim 3,
- wherein said database includes and associates imaged-site information, examination-type information, and the age or sex of the information subject, as items of characteristic information of said patient's medical image, and
- said searching unit searches said database, based on at least one or more of imaged-site information, examination-type information, or the age or sex of an information subject, for said patient's medical image.

5. The image-display device according to claim 3, further comprising a retention unit configured to retain a report acquired by interpreting said patient's medical image,
- wherein said searching unit acquires characteristic information of said patient's medical image from reports acquired by interpreting said patient's medical image.

6. The image-display device according to claim 3,
- wherein said searching unit predetermines a preference order and an information range for the characteristic information of said patient's medical image that has been acquired, and
- in the case that said associated medical image is not identified as a result of searching said database, searches again by expanding search ranges according to the preference order and the information ranges that have been predetermined.

7. The image-display device according to claim 1,
- wherein said database includes and associates post-surgery-image-identifying information, as one of the items of characteristic information, of the post-surgery medical image, and
- said searching unit searches said database, based on characteristics information of said patient's medical image and said post-surgery-image-identifying information.

8. The image-display device according to claim 7,
- wherein said database includes and associates examination-purpose information for the medical image as one of the items of characteristic information of the medical image, and
- said post-surgery-image-identifying information is said examination-purpose information that indicates a post-surgery check.

9. The image-display device according to claim 7,
- wherein said database includes and associates imaged-site information, examination-type information, and the age or sex of the information subject, as items of characteristic information of said patient's medical image, and
- said searching unit searches said database based on at least one or more of imaged-site information, examination-type information, or the age or sex of the information subject, for said patient's medical image.

10. The image-display device according to claim 7, further comprising a retention unit configured to retain a report acquired by interpreting said patient's medical image,
- wherein said searching unit acquires characteristic information of said patient's medical image from reports acquired by interpreting said patient's medical image.

11. The image-display device according to claim 7,
- wherein said searching unit predetermines a preference order and an information range for the characteristic information of said patient's medical image that has been acquired, and
- in the case that said associated medical image is not identified as a result of searching said database, searches again by expanding search ranges according to the preference order and the information ranges that have been predetermined.

12. An image-display system, comprising:
- an image-storage device configured to store medical images;
- a report-storage device configured to accumulate radiogram-interpretation reports for said medical images including a database in which, for each data item in the database, multiple items of characteristic information included in said radiogram-interpretation reports including established-disease name or examination purpose information are associated with information for identifying said medical images;
- a display unit configured to display a patient's medical image; and
- a searching unit configured to search from said database, a radiogram-interpretation report including at least one item of characteristic information which is the same as that of said patient's medical image and that indicates that established-disease-name-information indicates that a subject of the searched radiogram-interpretation report is able-bodied or that said examination-purpose information is post-surgery to identify a medical image related to the searched report in order to associate said identified medical image with said patient's medical image.

13. The image-display system according to claim 12, further comprising an image-acquisition unit configured to acquire associated medical images identified by said searching unit from said image-storage device,
- wherein said display unit simultaneously displays said medical image acquired by said image-acquisition unit and said patient's medical image.

* * * * *